United States Patent
Schreiner et al.

(10) Patent No.: US 8,716,539 B2
(45) Date of Patent: May 6, 2014

(54) METHOD FOR PRODUCING SUBSTITUTED DIAMANTANES

(75) Inventors: Peter R. Schreiner, Wettenberg (DE); Andrey A. Fokin, Giessen (DE)

(73) Assignee: Justus-Liebig-Universitaet Giessen, Giessen (DE)

( * ) Notice: Subject to any disclaimer, the term of this patent is extended or adjusted under 35 U.S.C. 154(b) by 704 days.

(21) Appl. No.: 12/086,058

(22) PCT Filed: Dec. 4, 2006

(86) PCT No.: PCT/DE2006/002146
§ 371 (c)(1),
(2), (4) Date: Oct. 29, 2009

(87) PCT Pub. No.: WO2007/065409
PCT Pub. Date: Jun. 14, 2007

(65) Prior Publication Data
US 2010/0036153 A1  Feb. 11, 2010

(30) Foreign Application Priority Data
Dec. 6, 2005 (DE) .......................... 10 2005 058 357

(51) Int. Cl.
C07C 13/28  (2006.01)

(52) U.S. Cl.
USPC ....................................................... 585/352

(58) Field of Classification Search
None
See application file for complete search history.

(56) References Cited

U.S. PATENT DOCUMENTS

| | | | |
|---|---|---|---|
| 5,410,092 | A | 4/1995 | Shen |
| 5,430,193 | A | 7/1995 | Shen |
| 2005/0074690 | A1 | 4/2005 | Liu et al. |

FOREIGN PATENT DOCUMENTS

| | | |
|---|---|---|
| WO | 02/057201 | 7/2002 |
| WO | 03/050066 | 6/2003 |

OTHER PUBLICATIONS

Y. Klimochkin et al., "Reactivity of cage hydrocarbons in the nitroxylation reaction", Petroleum Chemistry, vol. 40, No. 6, 454-457, 2000.
R. Duddu et al., "Nitronium ion mediated functionalization of adamantine and its derivatives", Synthetic Communications, 26(18), 3495-3501 (1996).
Y. Klimochkin et al., "Synthesis and hydrolytic conversions of nitroxy derivatives of homoadamantane, protoadamantane and bicycle[3.3.1]nonane", Russian Journal of Organic Chemistry, (1993), 29(7), 1358-1364.
T. Courtney et al., "The Chemistry of Diamantane. Part 1. Synthesis and Some Functionalisation Reactions" (1972) *J.C.S Perkin I*, 2691-2696.
T. Gund et al., "Diamantane.II. Preparation of Derivatives of Diamantane" (1974) *J. Org Chem.*, vol. 39(20), 2987-2994.
L. Vodicka et al., "Synthesis of Diamantanedicarboxylic Acids with the Carboxy Groups Bonded at Tertiary Carbon Atoms" (1983) *Collection Czechoslovak Chem. Commun.*, vol. 48, 1162-1172.
G. Olah et al., "Nitration of Adamantane and Diamantane with Nitronium Tetrafluoroborate" (1993) *J. American Chemical Soc.*, 115, 7246-7249.
F. Blaney et al., "Diamondoid Rearrangements in Chlorosulphonic Acid. A Highly Regioselective Route to Apically Disubstituted Diamantanes" (1975) *Tetrahadron Letters*, No. 2, 99-100.
A. Fokin et al., "Functionalized Nanodiamonds Part I. An Experimental Assessment of Diamantane and Computational Predictions for Higher Diamondoids" (2005) *Chem. Eur. J.*, 11, 7091-7101.
A. Fokin et al., "Reactivity of [1(2,3)4]Pentamantane ($T_d$-Pentamantane): A Nanoscale Model of Diamond" (2006) *J. Org. Chem.*, 71, 8532-8540.
M. Davis et al., "Preparation of Diamines of Adamantane and Diamantane from the Diazides" (2006) *Synthetic Communications*, 36, 2113-2119.
J. Janku, et al., "Hydrolysis of Bromine Derivatives of Diamantane with Nitric Acid" (1981) *Zeitschrift fuer Chemie*, 21(9), 325-326.
J. Janku, et al., "Diamantyl Methanols: Their Oxidation by Lead/IV/ Acetate" (1984), *Sbornik Vysoke Skoly Chemicko-Technologicke v Praze, D: Technologie Paliv*. D49, 5-23.
F. Blaney et al., "Hydroxylation of Diamantan-1- and -4-ol with the Fungus *Rhizopus nigricans*", *J.C.S. Chem. Comm.* 1974 (8), 297-298.

*Primary Examiner* — Sudhakar Katakam
(74) *Attorney, Agent, or Firm* — Clark & Brody

(57) ABSTRACT

Dinitroxylated diamantanes are suitable for being reacted with nucleophiles to form the corresponding disubstituted diamantanes. Surprisingly, at least dinitroxylated or hydroxylated diamantanes are rearranged in the presence of a strong acid and at least 4,9-nitroxylated or hydroxylated diamantanes are created. On this basis, 4,9-substituted diamantanes are able to be produced in a targeted manner by reaction with further nucleophiles. Methods for producing at least disubstituted diamantanes include: (a) at least dinitroxylation, followed by the substitution of all nitroxy groups by a nucleophile; or (b) at least dinitroxylation, the subsequent rearrangement in the presence of a strong acid, after realized rearrangement all nitroxy groups are replaced by a nucleophile; or (c) at least dinitroxylation, then subsequent reaction with water (as nucleophile), and rearrangement of the at least dihydroxylated compound in the presence of a strong acid, all hydroxy groups being replaced by another nucleophile in the event of a successful rearrangement.

25 Claims, No Drawings

METHOD FOR PRODUCING SUBSTITUTED DIAMANTANES

The present invention provides methods for the selective production of derivatised diamantanes, wherein the formation of product mixtures which are difficult to separate is avoided and yields of at least 60%, compared to the diamantane used as starting material, are obtained.

STATE OF THE ART

Diamantanes as starting substances are of interest for microelectronics, pharmaceutics, nanotechnology, and material sciences. Potential applications are, for instance, the production of temperature-stable plastics, coatings with tailored conductivities for LEDs and transistors, nanoelectronics, as well as application in pharmaceuticals against viral and neurodegenerative diseases.

Hereby, diamantanes with hydroxy groups, carbonyl groups, carboxyl groups, amino groups and/or aminocarbonyl groups are of particular interest as they are important intermediates for the production of oligomeric and polymeric diamantanes. Furthermore, the aforementioned functional groups are suitable for being substituted by other functional groups in such a way that substituted diamantanes represent important starting materials for the production of further substituted diamantanes.

The state of the art knows several methods for producing hydroxylated diamantanes. The methods known so far provide, however, only minor yields of hydroxylated diamantanes and/or require complex purification steps (for instance chromatography) and/or require the use of fine chemicals, i.e. highly pure solvents and reagents.

Thus, the oxidation of diamantane 1 in 96% sulphuric acid yields only 5% of the corresponding dihydroxy derivative 2, along with the main products 3 and 4 (Courtney, T.; Johnston, D. E.; McKervey, M. A.; Rooney, J. J. Chemistry of diamantane. I. Synthesis and functionalization reactions, Journal of the Chemical Society, Perkin Transactions 1: Organic and Bio-Organic Chemistry (1972-1999) (1972), (21), 2691-6). In this method, the yield of the desired product 2 is very poor and the resulting mixture is only able to be separated with a high effort.

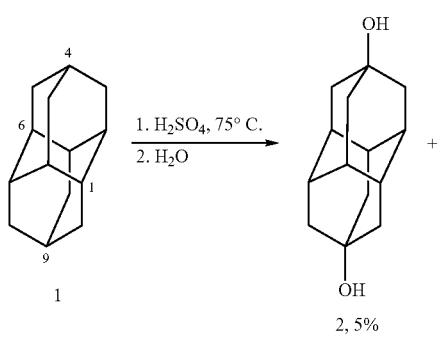

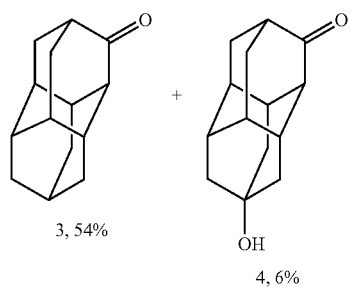

3, 54%

4, 6%

Reduction of the dimer of norbornadiene (Binor-S, 5) to a mixture of tetrahydro derivatives 6, subsequent reaction with pure chlorosulfonic acid and hydrolysis of the dichloride 7 in presence of NaOH in an autoclave also yields 4,9-dihydroxydiamantane 2 (Blaney, Frank; Johnston, Don E.; McKervey, M. Anthony; Rooney, John J. Diamondoid rearrangements in chlorosulfonic acid. Highly regioselective route to apically disubstituted diamantanes. Tetrahedron Letters (1975), (2), 99-100). Disadvantages of this method are the use of a starting material produced via several steps and the requirement of an autoclave reaction. Diamantane is able to be obtained in high quantities directly from petroleum. Thus, methods are preferred which use 1 as starting material for the synthesis of 3.

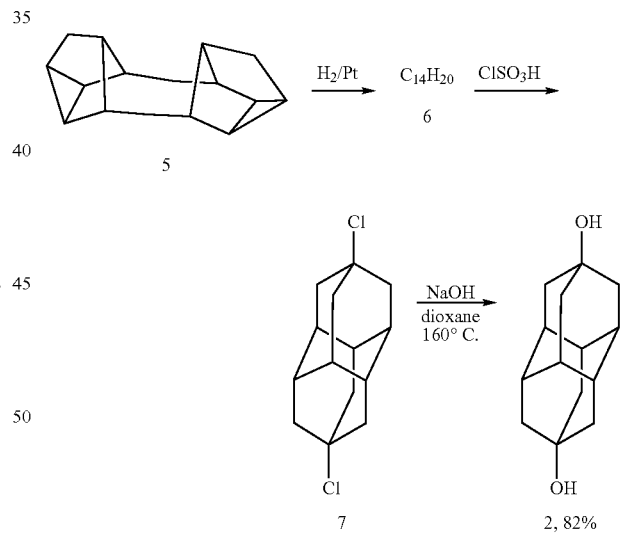

Oxidation of 4-hydroxydiamantane 8 with the fungus *Rhizopus nigricans* yields a mixture of 1,9-dihydroxydiamantane 9 and 4,9-dihydroxydiamantane 2 in a ratio of 5:1 in a yield of 69% (Blaney, Frank; Johnston, Don E.; McKervey, M. Anthony; Jones, Ewart R. H.; Pragnell, John. Hydroxylation of diamantan-1- and -4-ol with the fungus *Rhizopus nigricans*. Journal of the Chemical Society, Chemical Communications (1974), (8), 297-8). The disadvantage of this method is that 7, a very expensive starting material, is used and a mixture which is difficult to separate is obtained containing only approx. 15% of 2.

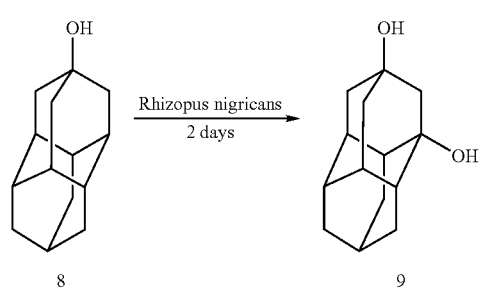

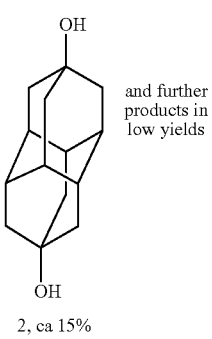

Bromination of diamantane to 4,9-dibromodiamantane 10, followed by a hydrolysis to 2 (Janku, Josef; Burkhard, Jiri; Vodicka, Ludek. Hydrolysis of bromine derivatives of diamantane with nitric acid. Zeitschrift fuer Chemie (1981), 21(9), 325-6). This method only occurs with low selectivity during the bromination and, thus, low yield of 3.

US 2005/0074690 A1 describes polymers comprising monomeric units of diamantanes. This patent specification describes a method for producing dihydroxylated to tetrahydroxylated diamantanes through reaction of diamantane with N-hydroxyphthalimide and Co-II-acetylacetonate. It is disadvantageous that a product mixture is formed and that the yield is low.

U.S. Pat. No. 5,430,193 and U.S. Pat. No. 5,410,092 describe methods to convert a diamantane lactone into the corresponding hydroxyketone, wherein the hydroxy group and the carbonyl group are separated by at least one bridgehead carbon atom. Hereby, the diamondoid lactone reacts with an anhydride in the presence of an acid and the keto ester formed as intermediate is hydrolysed. The selective introduction of functional groups into unsubstituted diamantanes is, however, not possible with this method.

WO 03/050066 A1 and WO 02/057201 A2 describe functionalised or polymerisable higher diamantanes. Neither patent specification gives, however, any reference to the production of the derivatised diamantanes. The oxidation of diamantane 1 with m-chloroperbenzoic acid or $HNO_3$ as oxidizing agent and $CH_2Cl_2$ as solvent is described in A A Fokin, B A Tkachenko, P A Guchenko, D V Gusev, P R Schreiner: Functionalized Nanodiamonds Part I. An Experimental Assessment of Diamantane and Computational Predictions for Higher Diamondoids. Chem. Eur. J. 2005, 11, 7091-7101. Upon use of nitric acid and subsequent conversion with water, a mixture of different monohydroxy diamantanes is formed (8 and 13); upon use of m-chloroperbenzoic acids, even mixtures of different mono- and dihydroxyadamantanes are formed.

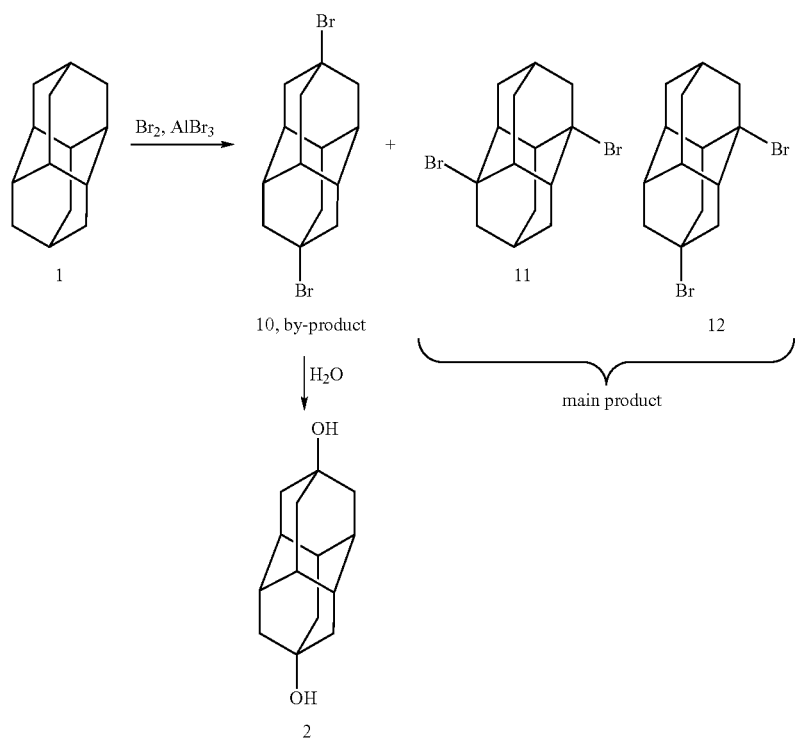

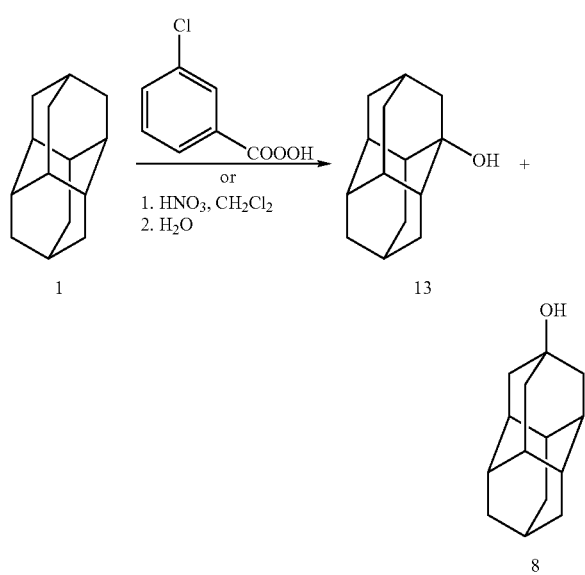

The invention at hand is characterised, compared to the state of the art, by the fact that it allows for the selective production of substituted diamantanes from the corresponding nitroxylated diamantanes.

Surprisingly it has been found that mononitroxylated diamantanes are suitable for being quenched by numerous nucleophiles and, hence, for being intermediates for producing monosubstituted diamantanes, and that the at least dinitroxylated diamanantes, so far not known to persons skilled in the art, are suitable for the selective production of at least diderivatised diamantanes.

The invention at hand, thus, provides new, at least disubstituted diamantanes not previously known.

Furthermore, the invention at hand provides methods for producing substituted diamantanes. Hereby, the diamantanes used as starting material are nitroxylated in a first step. The nitroxy group is a good leaving group and is, hence, easily suitable for being substituted by other nucleophiles. In a further step, the nitroxylated diamantanes are reacted with nucleophiles.

Surprisingly, it was found that in the case of at least a dinitroxylation, at least one nitroxy group is bound to one apical carbon atom of the diamantane.

Furthermore, within the framework of the work which resulted in the invention at hand, it was found that dinitroxylated as well as dihydroxylated diamantanes are rearranged in the presence of a strong acid, if one of the two nitroxy groups or hydroxy groups had been previously bound to an apical carbon atom. During this rearrangement, a nitroxy group or hydroxy group which had not been previously bound to an apical carbon atom migrates to an apical carbon atom onto which a hydrogen atom had been previously bound. The rearrangement product may subsequently react with further nucleophiles.

It is known to persons skilled in the art how to convert hydroxy groups into other functional groups. Thus, hydroxy compounds can be converted into the corresponding carboxylic acids via reaction with formic acid in concentrated sulfuric acid. This Koch-Haaf reaction is, for instance, described in L Vodicka, J Janku, J Burkhard: "Synthesis of diamantanedicarboxylic acid with the carboxy groups bonded at tertiary carbon atoms." Lab. Synth. Fuels, Prague Inst. Chem.-Technol., Prague, Czech. Collection of the Czechoslovak Chemical Communications (1983), 48 (4), 1162-1172. It is also known to persons skilled in the art that the Koch-Haaf reaction is also suitable for being used in order to convert nitroxylated compounds into the corresponding carboxylic acids. This reaction is described in T M Gund, M Nomura, PvR Schleyer, J. Org. Chem. 1974, 39, 2987-2994.

The introduction of alkylamino groups is known to persons skilled in the art and described, for instance, in A A Fokin, B A Tkachenko, P A Guchenko, D V Gusev, P R Schreiner: Functionalized Nanodiamonds Part I. An Experimental Assessment of Diamantane and Computational Predictions for Higher Diamondoids. Chem. Eur. J. 2005, 11, 7091-7101 based on the example of the conversion of brominated diamantanes with acetonitrile. It is known to persons skilled in the art that hydroxy groups and nitroxy groups are suitable to be converted in an analogous manner into alkylamino groups.

It is known to persons skilled in the art how to convert hydroxy groups and nitroxy groups into alkylcarboxylic acid esters, wherein OH— or —$ONO_2$-groups are substituted by OCO-alkyl-groups. The production of 1-acetoxy diamantane from 1-hydroxy diamantane and acetic acid is, for instance, described in J Janku, L Vodicka, J Jeziorsky. Sbornik Vysoke Skoly Chemicko-Technologicke v Praze, D: Technologie Paliv. 1984, D49, 5-23.

AIM OF THE INVENTION

It is the aim of the invention to provide at least dinitroxylated diamantanes as well as a method for their production. It is a further aim of the invention to improve the methods for producing substituted diamantanes wherein improvement is understood to be an increased yield and/or an increased selectivity of the product formation.

Achievement of this Aim

The at least dinitroxylated diamantanes according to the present invention have the following general structural formula

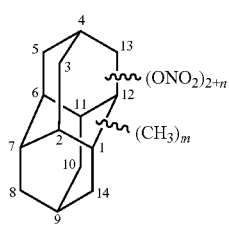

wherein n represents an integer between 0 and 6,
m represents an integer between 0 and 1,
the methyl group in the case of m=1 is bound preferably to position 1, 3 or 4 of the diamantane,
and at least one nitroxy group is bound to an apical carbon atom.

The aim to provide improved methods for producing substituted diamantanes is achieved, according to the present invention, by first converting 1 equivalent of the diamantane with 1.8 to 20.0 equivalents of a nitroxylating agent per nitroxy group to be introduced. Optionally, the reaction takes place in an organic solvent. The organic solvent is preferably selected from the group $CH_2Cl_2$, $CHCl_3$, $CCl_4$, diethylether, THF, ethyl acetate or mixtures thereof.

According to the present invention, the nitroxylated diamantanes are converted in a further step with one nucleophile, wherein the nucleophile substitutes all nitroxy groups.

Surprisingly, it was found that yield and/or selectivity of the production of at least disubstituted diamantanes are able to be significantly increased by at least dinitroxylating the diamantanes 1 at first and subsequently converting the product mixture formed hereby in presence of a nucleophile into the corresponding mixture of polysubstituted diamondoids. Hereby, the term substituted refers to such functional groups which are or have been introduced with only the help of the methods according to the present invention.

It has been found that during the at least dinitroxylation of diamantanes, at least one nitroxy group is bound in an apical position of the diamantane, i.e. in position 4 or 9. The nitroxy group is a good leaving group and is easily suitable for being substituted by other nucleophilic groups. It is known to persons skilled in the art how to introduce these nucleophiles. Furthermore, it is known that the product mixtures formed are able to be separated and purified, for instance, through extraction, recrystallisation or chromatography.

In a preferred embodiment of the invention at hand the at least dinitroxylated diamantane is rearranged in the presence of a strong acid. Surprisingly, it was found that at least dinitroxylated diamantanes, in which at least one nitroxy group is bound to an apical carbon atom, are rearranged when a strong acid is added. During this rearrangement, a nitroxy group which had not been previously bound to an apical carbon atom migrates to an apical carbon atom to which a hydrogen atom had been previously bound. Alternatively, the at least dinitroxylated diamantanes, which carry at least one apical nitroxy group, are suitable for being first hydrolysed with water (as nucleophile) and subsequently rearranged in the presence of a strong acid. Within the framework of the invention at hand, it has been found that not only dinitroxydiamantanes, but also dihydroxydiamantanes are rearranged in the presence of a strong acid, if at least one apical nitroxy group or dihydroxy group had been previously bound to an apical carbon atom.

Nitrated compounds are, in contrast, not capable of performing the aforementioned rearrangement reaction. It is known to persons skilled in the art that, according to the current state of the art, there is no possibility of converting the nitro group —$NO_2$ into a nitroxy group —$ONO_2$. The at least dinitroxylation according to the present invention is, thus, the decisive step in the production of at least disubstituted diamantanes with high yield and/or selectivity.

The acid rearrangement of at least dinitroxylated diamantanes is shown as an example, but not exhaustively, for 1,4-dinitroxydiamantane 16:

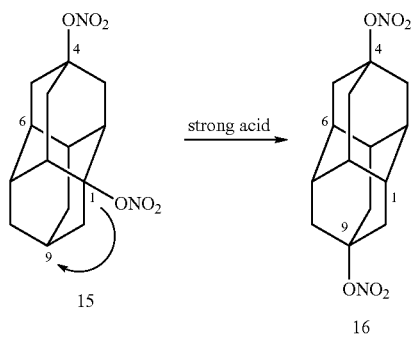

The acid rearrangement of at least dihydroxylated diamantanes is shown as an example, but not exhaustively, for 1,4-dihydroxydiamantane 2:

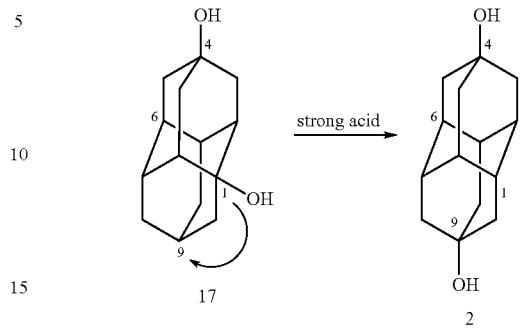

The following methods according to the present invention are at the disposal of persons skilled in the art for the production of at least disubstituted diamantanes:
a) at least dinitroxylation, followed by the substitution of all nitroxy groups by a nucleophile or
b) at least dinitroxylation, subsequent rearrangement in the presence of a strong acid, after realised rearrangement all nitroxy groups are replaced by a nucleophile or
c) at least dinitroxylation, subsequent reaction with water (as nucleophile), rearrangement of the at least dihydroxylated compound in the presence of a strong acid, after realised rearrangement all hydroxy groups are replaced by another nucleophile.

The methods according to the present invention for producing at least disubstituted diamondoids are described in the following:

1. Production of at Least Dinitroxylated Diamondoids

The production of the at least dinitroxylated diamondoids according to the method of the present invention is carried out according to the following general instruction.

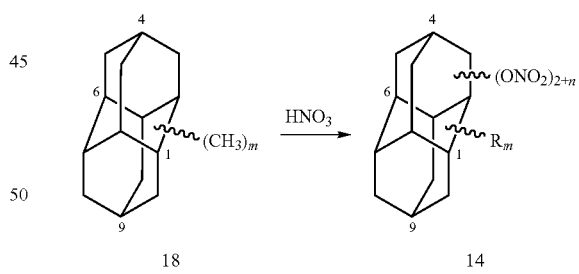

Hereby m, n and R are defined as described on page 8.

1 mol of the diamondoid 18 is mixed with 0 to 2 liters of a non-polar organic solvent and 8 mol to 25 mol of a nitroxylating agent per nitroxy group to be introduced at −5° C. to 5 C and stirred for 1 h to 3 h at 20° C. to 30° C.

The crude product 14 is suitable for being directly post-processed or for being optionally isolated.

In the latter, excess acid is quenched with solid $NaHCO_3$. The precipitate formed hereby is filtered and the non-polar organic solvent is removed at reduced pressure.

Diamantanes, in the sense of the present invention, are, for instance, diamantane and their mono- or multi-alkylsubstituted derivatives.

An organic solvent selected from the group of halogenated hydrocarbon with one to two C atoms, preferably methylene chloride, chloroform, carbon tetrachloride, diethylether, tetrahydrofuran, ethyl acetate or a mixture thereof, is preferably used in the nitration.

Concentrated nitric acid with w $(HNO_3)$=75% to 100% or a precursor of the concentrated nitric acid is understood within the framework of the invention at hand under "nitroxylating agent". Precursors of the concentrated nitric acid are, for instance, mixtures of concentrated sulphuric acid with w $(H_2SO_4) \geq 96\%$ and at least one alkali metal nitrate, for instance lithium nitrate, sodium nitrate, potassium nitrate or mixtures from ozone and nitrogen dioxide or $NO^+X^-$ and $NO_2^+X^-$ reagents, wherein X is a halogen selected from fluorine, chlorine, bromine, iodine. It is known to persons skilled in the art how to convert these precursors of the concentrated nitric acid into the concentrated nitric acid.

2. Rearrangement of at Least Dinitroxylated Diamantanes and Subsequent Reaction with Water

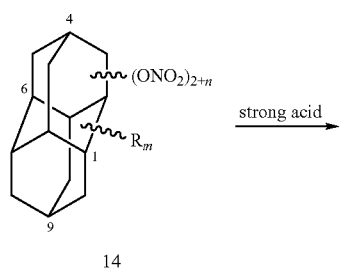

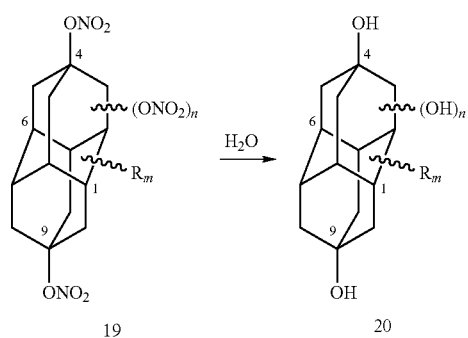

The crude product 14 is added to a concentrated strong acid, wherein per nitroxy group of the crude product 14 used as starting material, 1.5 mol to 5 mol acid, respectively, are used. It is stirred 1 h to 3 h at 20° C. to 30° C. Subsequently, the reaction mixture 19 is poured onto ice (1 to 3 parts by volume of ice for every part of volume of the reaction mixture) and optionally filtrated.

Subsequently the reaction product 20 is purified, wherein the purification is carried out by means of chromatography, recrystallisation, discontinuous or continuous extraction.

3. Rearrangement of at Least Dinitroxylated Diamantanes with Water and Subsequent Reaction

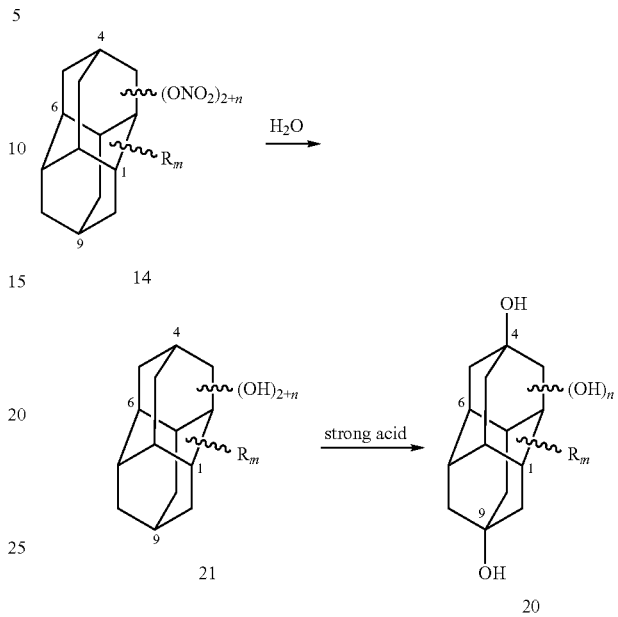

The crude product 14 is diluted after stirring at 20° C. to 30° C. with water in the ratio reaction mixture:water=1:0.3 to 1:0.7. The organic solvent is removed and the remaining aqueous phase is refluxed for 1 h to 2 h. Then the reaction mixture is cooled to 20° C. to 30° C. and filtrated. The remainder consisting of a mixture of different hydroxylated diamantanes 21 is added to a concentrated strong acid, wherein per nitroxy group of the crude product 14 used as starting material, 1.5 mol to 5 mol acid, respectively, are used. It is stirred for 1 h to 3 h at 20° C. to 30° C. Subsequently, the reaction mixture 20 is poured onto ice (1 to 2 parts by volume ice for every part of volume of the reaction mixture) and optionally filtered.

Optionally, the rearrangement in the presence of a concentrated strong acid can be foregone.

Subsequently, the reaction product 20 is purified, wherein the purification is carried by means of chromatography, recrystallisation, discontinuous or continuous extraction.

It is known to persons skilled in the art that strong acids are such acids whose $pK_a$ value is smaller or equal to 2. For the rearrangement reaction, strong acids, such as, but not exhaustively, sulphuric acid, hydrochloric acid, hydrobromic acid, hydroiodic acid, nitric acid, phosphoric acid and trifluoroacetic acid are suitable. The strong acid is preferably used in concentrated form, wherein such solvents of strong acids, whose pH value is smaller or equal to zero, are understood under "concentrated".

The optional filtration after rearrangement is preferably carried out through a glass or porcelain frit.

The optional purification of the product is carried out by recrystallisation, chromatography, or extraction.

In the case of recrystallisation, a solvent is used which is selected from the group of aliphatic chain-type or cyclic ethers with two to fourteen C atoms, halogenated hydrocarbons with one to two C atoms, aliphatic chain-type or cyclic hydrocarbons with four to fourteen C atoms, aromatic or araliphatic hydrocarbons with six to fourteen C atoms and their mixtures. If the purification is carried out by means of extraction, at least one organic solvent is used as a means of extraction, selected from the group of aliphatic chain-type or cyclic ethers with two to fourteen C atoms, halogenated hydrocarbons with one to two C atoms, aliphatic chain-type or cyclic hydrocarbons with four to fourteen C atoms, aromatic or araliphatic hydrocarbons with six to fourteen C atoms and their mixtures.

It is known to persons skilled in the art how to convert $ONO_2$— or OH-groups into other functional groups by means of nucleophilic substitution. As an example, but not exhaustively, —$NHCOCH_3$, —COOH, —NHCOOH as functional groups are named here, for instance, and $CH_3COOH$, HCOOH, $CH_3CN$, $H_2O$, $HCONH_2$ as nucleophiles. Water itself serves, furthermore, in the framework of the invention at hand also as nucleophile, suitable for substituting the —$ONO_2$-groups.

Diamantane derivatives are used, for instance, in pharmacology, microelectronics and the material sciences. In pharmacology, they are suitable for being used for pharmacophore-based drug design, combinatorial drug discovery, drug delivery and for diagnostics. In microelectronics, diamondoids are suitable materials for inflexible, durable electronic components in the nanometer scale, for applications in the area of field emission, for sensors, for the controlled introduction of doping substances such as N, P, B in the semiconductor technology as well as growth seed in the production of artificial diamants. Furthermore, diamondoids find application in material sciences, for instance for surface films, coatings and polymers.

For persons skilled in the art, it is obviously clear that the reaction sequence of at least dinitroxylation and subsequent rearrangement is also suitable for the production of other diamondoids, for instance for adamantane, triamantane, tetramantane, pentamantane, hexamantane, heptamantane, octamantane, nonamantane and decamantane.

EMBODIMENTS

Embodiment 1

Production of 1-nitroxydiamantane

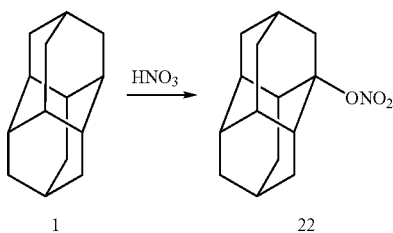

Diamantane 1 (19.3 g; 0.103 mol), $CH_2Cl_2$ (100 mL) and 99% $HNO_3$ (38.5 mL; 0.91 mol) are mixed at 0° C., stirred for 30 minutes at 20° C., cooled to 0° C. and the excess acid is neutralised with solid $NaHCO_3$. The precipitate is filtrated and $CH_2Cl_2$ removed at reduced pressure. The remaining remainder after removal of $CH_2Cl_2$ is recrystallised from n-hexane and yields 21.7 g (85%) 1-nitroxydiamantane 22.

$^1$H-NMR: (400 MHz, δ, ppm, $CDCl_3$): 2.30 bs (2H), 2.15 bs (3H), 2.05 m (6H), 1.68 m (4H), 1.60 m (2H), 1.47 m (2H).

$^{13}$C-NMR: (100 MHz, δ, ppm, $CDCl_3$): 93.7 (C), 40.5 (CH), 39.3 ($CH_2$), 39.2 (CH), 37.5 ($CH_2$), 36.7 ($CH_2$), 36.3 (CH), 32.3 ($CH_2$), 30.3 (CH), 24.6 (CH).

Characteristic bands in the IR spectrum: (ν, cm$^{-1}$, $CHCl_3$): 2997 (C—H), 2855 (C—H), 1611 (N=O), 1306 (N=O), 1247 (C—O).

Embodiment 2

Production of 1-acetaminodiamantane

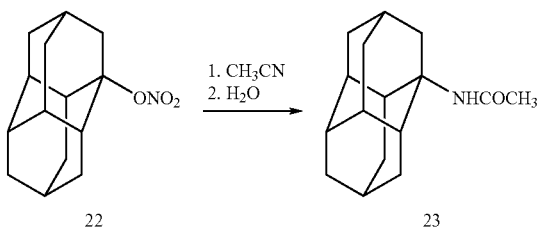

1 g (4.0 mmol) 1-nitroxy diamantane 22 is dissolved in 100 mL acetonitrile. The reaction mixture is heated to reflux for 10 h and subsequently cooled to room temperature. Then 1 mL water is added. After removal of the volatile components at reduced pressure, the remainder of $CCl_4$ is recrystallised. 0.78 g (79%) of 1-acetaminodiamantane 23 yield.

$^1$H-NMR: (400 MHz, δ, ppm, $CDCl_3$): 5.50 (brs, 1H), 2.22 (m, 2H), 2.03 (m, 2H), 1.93 (m, 4H), 1.90 (s, 4H), 1.49 (m, 2H), 1.45 (m, 8H).

$^{13}$C-NMR: (100 MHz, δ, ppm, $CDCl_3$): 169.1, 56.1, 41.5, 39.1, 38.7, 38.1, 37.3, 37.0, 32.8, 28.6, 25.1, 24.5. MS (70 eV) (m/z, %): 245 (71), 230 (14), 202 (7), 186 (94), 171 (4), 157 (6), 143 (11), 130 (45), 129 (41), 95 (90), 94 (100), 79 (25), 67 (18), 53 (11).

Embodiment 3

Production of 1-diamantane Carboxylic Acid

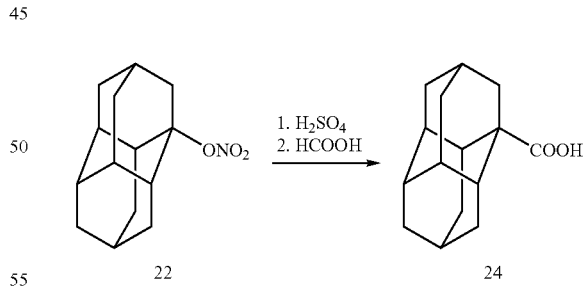

1 g (4.0 mmol) 1-nitroxy diamantane 22 is added at a temperature of 10° C. under stirring to a mixture of 25 mL of 98% $H_2SO_4$ and 2 mL formic acid. Additionally, at this temperature during 1 h a further 3 mL formic acid are added. The reaction mixture is poured onto 100 g ice and extracted three times with 20 mL chloroform, respectively. The combined extracts are first washed with water, subsequently with brine and dried over $Na_2SO_4$. Removal of the solvent at reduced pressure and subsequent recrystallisation of the remainder of $CHCl_3$ yield 0.75 g (81%) 1-diamantane carboxylic acid 24.

Embodiment 4

Production of 1-acetoxy Diamantane

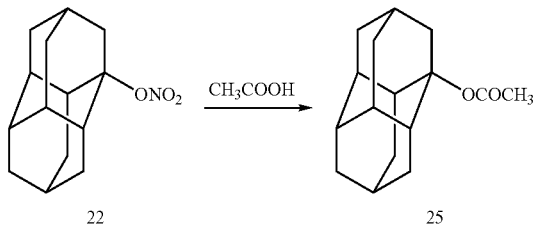

1 g (4.0 mmol) 1-nitroxy diamantane 22 is dissolved in 10 mL acetic acid. The reaction mixture is stirred for 10 h at 70° C., cooled to room temperature, diluted with 30 mL water and extracted three times with 10 mL chloroform, respectively. The combined extracts are first washed with water, subsequently with brine and dried over $Na_2SO_4$. Removal of the solvent at reduced pressure and recrystallisation of the remainder of n-hexane yield 0.88 g (89%) 1-acetoxy diamanatante 25.

Embodiment 5

Production of 1-hydroxy Diamantane

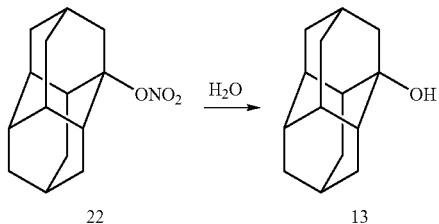

1 g (4.0 mmol) 1-nitroxy diamantane 22 is dissolved in 4 mL of 30% nitric acid and heated to reflux for 3 h. The reaction mixture is cooled and filtered. The precipitate is dried in the vacuum and recrystallised from cyclo hexane. 0.73 g (90%) of 1-hydroxy diamantane 13 yield.

Embodiment 6

Production of 1-dinitroxydiamantane

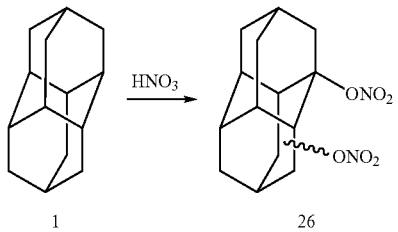

Diamantane 1 (10 g, 0.053 mol), $CH_2Cl_2$ (130 mL) and 99% $HNO_3$ (57 mL, 1.35 mol) are mixed at 0° C., stirred for 10 h at 25° C., cooled to 0° C. and the excess acid is neutralised with solid $NaHCO_3$. The precipitate is filtrated and $CH_2Cl_2$ removed at reduced pressure. The remainder remaining after removal of $CH_2Cl_2$ contains a mixture of dinitroxydiamantantes 26 (16.1 g; 97%).

$^1$H-NMR: (400 MHz, δ, ppm, $CDCl_3$): 2.40-2.00 m, 1.91-1.35 m.

Characteristic signals of the C—$ONO_2$-group in the $^{13}$C-NMR: (100 MHz, δ, ppm, $CDCl_3$): 93.7 (C), 91.9 (C), 90.5 (C), 87.9 (C).

Characteristic bands in the IR spectrum (ν, $cm^{-1}$, $CHCl_3$): 2990 (C—H), 2860 (C—H), 1610 (N=O), 1306 (N=O), 1250 (C—O), 1245 (C—O).

Embodiment 7

Rearrangement and Hydrolysis of Dinitroxydiamanantane

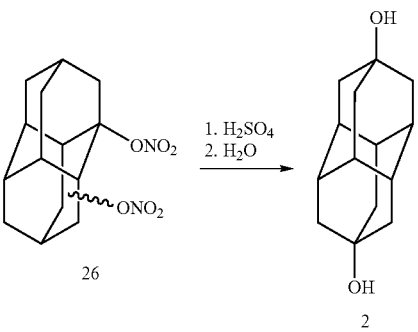

5 g of the mixture of the dinitroxydiamanantanes 26 are added at 0° C. to 100 mL of a 98% $H_2SO_4$ and subsequently stirred for 2.5 h at room temperature. Then, the reaction mixture is poured onto 300 g ice. Extraction with chloroform, removal of the solvent at reduced pressure and recrystallisation of the remainder from methanol yield 2.5 g (71%) 4,0-dihydroxydiamantane 2 in the form of a colourless solid, melting point 291-293° C. (literature 290-292° C.)

Embodiment 8

Hydrolysis and Rearrangement of Dinitroxydiamantane

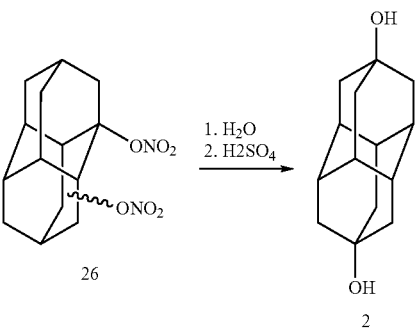

Diamantane 1 (1.28 g, 0.149 mol), $CH_2Cl_2$ (250 mL) and 100% $HNO_3$ (90 mL, 2.13 mol) are mixed at 0° C., stirred for 2 h at 25° C. and subsequently diluted with water (180 mL).

The CH$_2$Cl$_2$ is removed and the reaction mixture 26 is refluxed for 1.5 h. Removal of the water in the vacuum yielded a mixture of different oligohydroxydes 20 as a remainder. These 20 are added to 200 mL of 96% H$_2$SO$_4$ and stirred for 2 h at room temperature. Subsequently, the reaction mixture is poured onto 300 g ice and filtered. Extraction of the filtrate with one or several organic solvents (typically diethylether) yields 21.3 g (0.097 mmol, 65%) 4.9-dihydroxydiamantane (2, m=0) as white solid, mp. 291-293° C. (from methanol, literature 290-292° C.).

The invention claimed is:

1. Compound of the formula

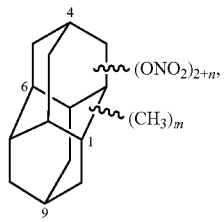

wherein n represents an integer between 0 and 6,
m represents an integer between 0 or 1,
the methyl group in the case of m=1 is bound to position 1, 3 or 4 of the diamantane,
and at least one nitroxy group is bound to an apical carbon atom.

2. Method for producing at least dinitroxylated diamantanes, characterised by the steps
a) mixture of the diamantane to be nitroxylated with a nitroxylating agent at −5° C. to 5° C. in the ratio of substance amounts diamantane:nitroxylating agent=1:8 to 1:25 per nitroxy group to be introduced,
b) stirring at 20° C. to 30° C. for 1 h to 3 h.

3. Method according to claim 2, wherein sulphonitric acid or concentrated nitric acid is used as nitroxylating agent.

4. Method according to claim 2, wherein a precursor of the concentrated nitric acid is used as nitroxylating agent, preferably a mixture of concentrated sulphuric acid or a mixture of ozone and nitrogen dioxide, NO$^+$X$^-$ and NO$_2^+$X$^-$ reagents, wherein X represents a halogen selected from fluorine, chlorine, bromine, iodine.

5. Method according to claim 2, wherein in step a) is used additionally an organic solvent selected from the group CH$_2$Cl$_2$, CHCl$_3$, CCl$_4$, diethylether, THF, ethyl acetate or a mixture thereof.

6. Method for producing at least disubstituted diamantanes, characterised by the steps
a) production of a at least dinitroxylated diamantane according to claim 2,
b) reaction of the at least dinitroxylated diamantane with a nucleophile.

7. Method for producing at least disubstituted diamantanes according to claim 6, wherein the nucleophile is selected from the group H$_2$O, HCOOH, CH$_3$COOH, HCONH$_2$, CH$_3$CN.

8. Method for producing at least dihydroxylated diamantanes, characterised by the steps
a) production of at least dinitroxylated diamantane according to claim 2,
b) addition of water,
c) heating to reflux for 1 h to 2 h,
d) addition of 1.5 to 5 mol of a strong concentrated acid per nitroxy group which had been introduced according to step a),
e) stirring for 1 h to 3 h at 20° C. to 30° C.,
f) addition of 1 part by volume of the reaction mixture, respectively, from step e) to 1 to 2 parts by volume of ice.

9. Method for producing at least dihydroxylated diamantanes according to claim 8, wherein the nitroxylation is carried out in the presence of one non-polar organic solvent selected from the group CH$_2$Cl$_2$, CHCl$_3$, CCl$_4$, diethylether, THF, ethyl acetate or a mixture thereof and this solvent is removed after addition of water and before heating to reflux.

10. Method for producing at least dihydroxylated diamantanes, characterised by the steps
a) production of a at least dinitroxylated diamantane according to claim 2,
b) addition of 1.5 to 5 mol of a strong concentrated acid per nitroxy group which had been introduced according to step a),
c) stirring at 20° C. to 30° C. for 1 h to 3 h,
d) addition of the reaction mixture from step c) to 1 to 3 parts by volume ice for every part of volume of the reaction mixture.

11. Method for producing at least dihydroxylated diamantanes according to claim 10, wherein the nitroxylation is carried out in the presence of a non-polar organic solvent selected from the group CH$_2$Cl$_2$, CHCl$_3$, CCl$_4$, diethylether, THF, ethyl acetate or a mixture thereof.

12. Method for producing at least dihydroxylated diamantanes according to claim 8, wherein the reaction mixture is filtered subsequently to the addition to ice.

13. Method for producing at least dihydroxylated diamantanes according to claim 8, wherein the strong concentrated acid in step e) is selected from the group sulphuric acid, hydrochloric acid, hydrobromic acid, hydroiodic acid, nitric acid, phosphoric acid.

14. Method for producing at least disubstituted diamantanes, characterised by the steps
a) production of a at least dinitroxylated diamantane according to claim 2,
b) reaction of the reaction mixture with a nucleophile selected from the group HCOOH, CH$_3$COOH, HCONH$_2$, CH$_3$CN.

15. Method for producing at least disubstituted diamantanes, characterised by the steps
c) production of a at least dinitroxylated diamantane according to claim 2,
d) addition of 1.5 to 5 mol of a strong concentrated acid per nitroxy group which had been introduced according to step a),
e) stirring at 20° C. to 30° C. for 1 h to 3 h,
f) reaction of the reaction mixture from step c) with a nucleophile selected from the group HCOOH, CH$_3$COOH, HCONH$_2$, CH$_3$CN.

16. Method for producing at least disubstituted diamantanes, characterised by the steps
a) production of a at least dinitroxylated diamantane according to claim 8,
b) reaction of the dihydroxylated diamantane with a nucleophile selected from the group HCOOH, CH$_3$COOH, HCONH$_2$, CH$_3$CN.

17. Method for producing substituted diamantanes according to claim 8, wherein additionally, and as the final step, purification of the product is carried out.

18. Method for producing substituted diamantanes according to claim 17, wherein the purification is carried out by means of chromatography.

19. Method for producing substituted diamantanes according to claim 17, wherein the purification is carried out by means of recrystallisation.

20. Method for producing substituted diamantanes according to claim 19, wherein, for the recrystallisation, a solvent is used which is selected from the group of aliphatic chain-type or cyclic ethers with two to fourteen C atoms, halogenated hydrocarbons with one to two C atoms, aliphatic chain-type or cyclic hydrocarbons with four to fourteen C atoms, aromatic or araliphatic hydrocarbons with six to fourteen C atoms and their mixtures.

21. Method for producing substituted diamantanes according to claim 17, wherein the purification is carried out by means of extraction with at least one organic solvent as extraction means.

22. Method according to claim 21, wherein the means of extraction is selected from the group of aliphatic chain-type or cyclic ethers with two to fourteen C atoms, halogenated hydrocarbons with one to two C atoms, aliphatic chain-type or cyclic hydrocarbons with four to fourteen C atoms, aromatic or araliphatic hydrocarbons with six to fourteen C atoms and their mixtures.

23. Method according to claim 21, wherein the extraction is carried out discontinuously.

24. Method according to claim 21, wherein the extraction is carried out continuously.

25. At least dihydroxylated diamantane which is able to be obtained by a method according to claim 8.

\* \* \* \* \*